(12) United States Patent
Kwak et al.

(10) Patent No.: US 8,313,512 B2
(45) Date of Patent: *Nov. 20, 2012

(54) S-SHAPED INTERSPINOUS PROCESS SPACER HAVING TIGHT ACCESS OFFSET HOOKS

(75) Inventors: Seungkyu Daniel Kwak, Needham, MA (US); Mark Gracia, Rochester, MA (US); John Riley Hawkins, Cumberland, RI (US); Lisa Gilman, Canton, MA (US); John Griffin, Boston, MA (US); Martin A. Reynolds, Mansfield, MA (US); Hassan Serhan, South Easton, MA (US)

(73) Assignee: DePuy Spine, Inc., Raynham, MA (US)

( * ) Notice: Subject to any disclaimer, the term of this patent is extended or adjusted under 35 U.S.C. 154(b) by 381 days.

This patent is subject to a terminal disclaimer.

(21) Appl. No.: 12/239,631

(22) Filed: Sep. 26, 2008

(65) Prior Publication Data

US 2009/0248079 A1    Oct. 1, 2009

Related U.S. Application Data

(63) Continuation-in-part of application No. 12/055,757, filed on Mar. 26, 2008.

(51) Int. Cl.
*A61B 17/70* (2006.01)
(52) U.S. Cl. ........................................................ 606/249
(58) Field of Classification Search .......... 606/246–253, 606/276–278, 324, 90, 105, 210–211, 214, 606/218–219, 235, 242; 403/97, 398, 157, 403/159; 24/370, 372–374; 294/26, 104, 294/16; 224/401, 440, 443, 446, 448, 451, 224/454, 456, 461
See application file for complete search history.

(56) References Cited

U.S. PATENT DOCUMENTS

| | | | |
|---|---|---|---|
| 5,007,909 A | 4/1991 | Rogozinski |
| 5,010,879 A | 4/1991 | Moriya |
| 5,074,864 A | 12/1991 | Cozad |
| 5,084,049 A | 1/1992 | Asher |
| 5,092,889 A | 3/1992 | Campbell, Jr. |
| 5,112,332 A | 5/1992 | Cozad |
| 5,116,334 A | 5/1992 | Cozad |
| 5,147,359 A | 9/1992 | Cozad |
| 5,246,442 A | 9/1993 | Ashman |
| 5,263,954 A | 11/1993 | Schlapfer |
| 5,282,801 A | 2/1994 | Sherman |
| 5,330,472 A | 7/1994 | Metz Stavenhagen |
| 5,380,325 A | 1/1995 | Lahille |
| 5,382,248 A | 1/1995 | Jacobson |
| 5,393,036 A | 2/1995 | Sheridan |
| 5,395,370 A | 3/1995 | Muller |
| 5,423,818 A | 6/1995 | Van Hoeck |
| 5,487,742 A | 1/1996 | Cotrel |
| 5,496,318 A | 3/1996 | Howland |
| 5,527,314 A | 6/1996 | Brumfield |
| 5,562,662 A | 10/1996 | Brumfield |

(Continued)

FOREIGN PATENT DOCUMENTS

EP        284559 A1      9/1988

(Continued)

*Primary Examiner* — Alvin Stewart
*Assistant Examiner* — Nicholas Plionis

(57) ABSTRACT

An S-shaped interspinous spacer having a pair of hooks that, upon lateral insertion between opposed spinous process, bear upon the opposed spinous processes.

4 Claims, 13 Drawing Sheets

U.S. PATENT DOCUMENTS

| | | | |
|---|---|---|---|
| 5,601,552 | A | 2/1997 | Cotrel |
| 5,609,592 | A | 3/1997 | Brumfield |
| 5,609,634 | A | 3/1997 | Voydeville |
| 5,620,444 | A | 4/1997 | Assaker |
| 5,651,789 | A | 7/1997 | Cotrel |
| 5,676,665 | A | 10/1997 | Bryan |
| 5,688,273 | A | 11/1997 | Errico |
| 5,688,274 | A | 11/1997 | Errico |
| 5,704,936 | A | 1/1998 | Mazel |
| 5,741,254 | A | 4/1998 | Henry |
| 5,743,911 | A | 4/1998 | Cotrel |
| 5,989,250 | A | 11/1999 | Wagner |
| 5,989,251 | A | 11/1999 | Nichols |
| 6,068,630 | A | 5/2000 | Zucherman |
| 6,074,391 | A | 6/2000 | Metz-Stavenhagen |
| 6,132,430 | A | 10/2000 | Wagner |
| 6,136,000 | A | 10/2000 | Louis |
| 6,416,515 | B1 | 7/2002 | Wagner |
| 6,451,019 | B1 | 9/2002 | Zucherman |
| 6,451,020 | B1 | 9/2002 | Zucherman |
| 6,458,131 | B1 | 10/2002 | Ray |
| 6,475,218 | B2 | 11/2002 | Gournay |
| 6,500,116 | B1 | 12/2002 | Knapp |
| 6,562,040 | B1 | 5/2003 | Wagner |
| 6,589,243 | B1 | 7/2003 | Viart |
| 6,626,908 | B2 | 9/2003 | Cooper |
| 6,641,585 | B2 | 11/2003 | Sato |
| 6,652,527 | B2 | 11/2003 | Zucherman |
| 6,761,720 | B1 * | 7/2004 | Senegas ............... 606/249 |
| 6,858,029 | B2 | 2/2005 | Yeh |
| 7,011,659 | B2 | 3/2006 | Lewis |
| 7,029,472 | B1 | 4/2006 | Fortin |
| 7,033,472 | B2 | 4/2006 | Yamanaka |
| 7,201,751 | B2 | 4/2007 | Zucherman |
| 2003/0032959 | A1 * | 2/2003 | Yeh ........................ 606/61 |
| 2003/0229345 | A1 * | 12/2003 | Stahurski ............... 606/61 |
| 2004/0064140 | A1 * | 4/2004 | Taylor et al. ............ 606/61 |
| 2004/0097931 | A1 | 5/2004 | Mitchell |
| 2004/0111091 | A1 | 6/2004 | Ogilvie |
| 2004/0186472 | A1 | 9/2004 | Lewis |
| 2004/0260285 | A1 | 12/2004 | Steib |
| 2005/0240182 | A1 | 10/2005 | Zucherman |
| 2006/0015099 | A1 | 1/2006 | Cannon |
| 2006/0229607 | A1 | 10/2006 | Brumfield |
| 2006/0241601 | A1 | 10/2006 | Trautwein |
| 2006/0293660 | A1 | 12/2006 | Lewis |
| 2007/0016189 | A1 | 1/2007 | Lake |
| 2007/0083201 | A1 | 4/2007 | Jones |
| 2007/0161992 | A1 * | 7/2007 | Kwak et al. ............ 606/61 |
| 2007/0162000 | A1 | 7/2007 | Perkins |
| 2007/0203468 | A1 | 8/2007 | Inoue |
| 2007/0270840 | A1 * | 11/2007 | Chin et al. ............ 606/61 |
| 2008/0033445 | A1 | 2/2008 | Zucherman |
| 2008/0045949 | A1 | 2/2008 | Hunt |
| 2008/0058806 | A1 * | 3/2008 | Klyce et al. ............ 606/61 |
| 2008/0058807 | A1 | 3/2008 | Klyce |
| 2008/0058808 | A1 | 3/2008 | Klyce |
| 2008/0058941 | A1 | 3/2008 | Zucherman |
| 2008/0065086 | A1 | 3/2008 | Zucherman |
| 2008/0086212 | A1 | 4/2008 | Zucherman |
| 2008/0167655 | A1 | 7/2008 | Wang |
| 2008/0167656 | A1 | 7/2008 | Zucherman |
| 2008/0177271 | A1 | 7/2008 | Yeh |
| 2008/0288075 | A1 | 11/2008 | Zucherman |
| 2009/0062918 | A1 * | 3/2009 | Wang et al. ............ 623/17.16 |
| 2009/0248076 | A1 | 10/2009 | Reynolds |

FOREIGN PATENT DOCUMENTS

| | | |
|---|---|---|
| EP | 446092 B1 | 7/1995 |
| EP | 535623 B1 | 3/1997 |
| EP | 1334703 B1 | 8/2006 |
| WO | 9423660 A1 | 10/1994 |
| WO | 9621396 A1 | 7/1996 |
| WO | 9725931 A1 | 7/1997 |
| WO | 9918877 A1 | 4/1999 |
| WO | WO 2007146928 | 12/2007 |

* cited by examiner

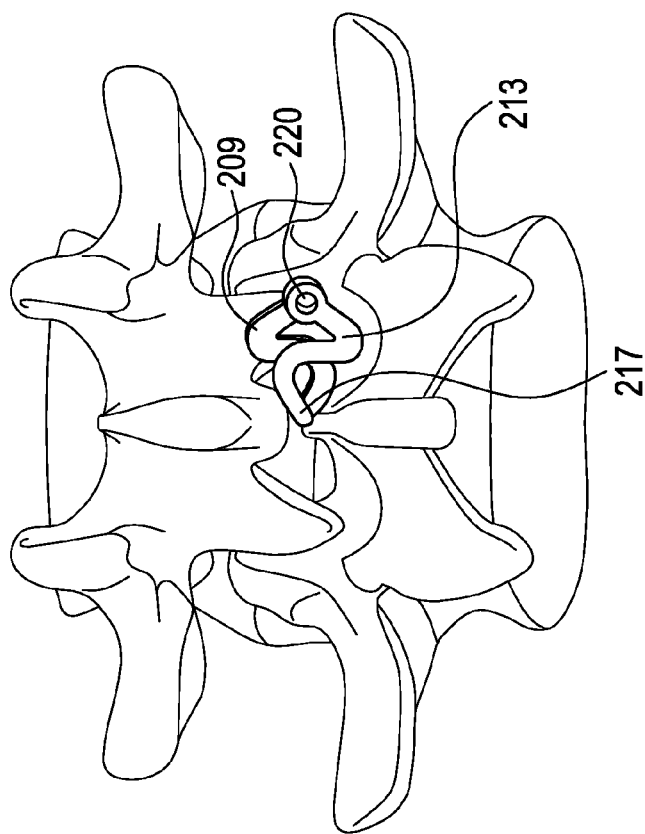
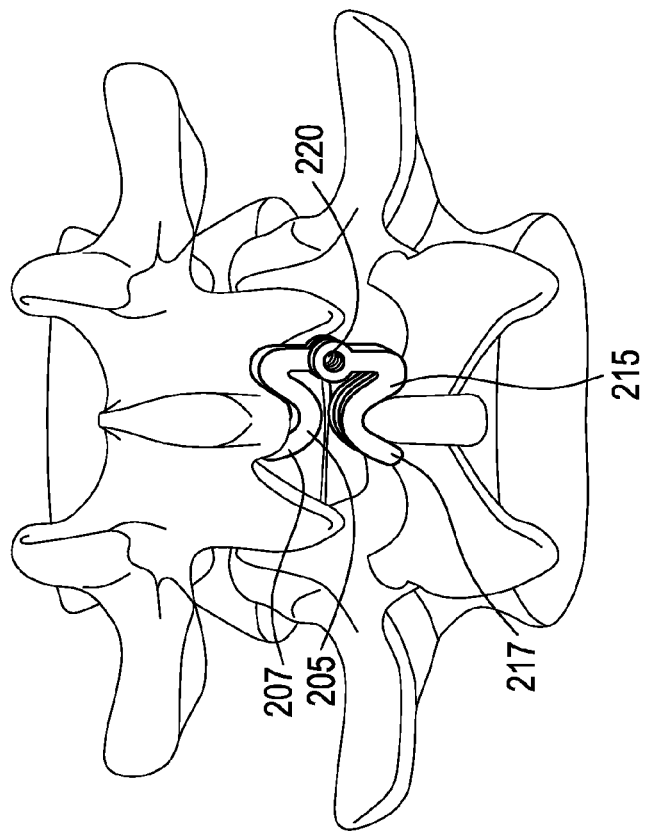
FIG. 9A
FIG. 9B

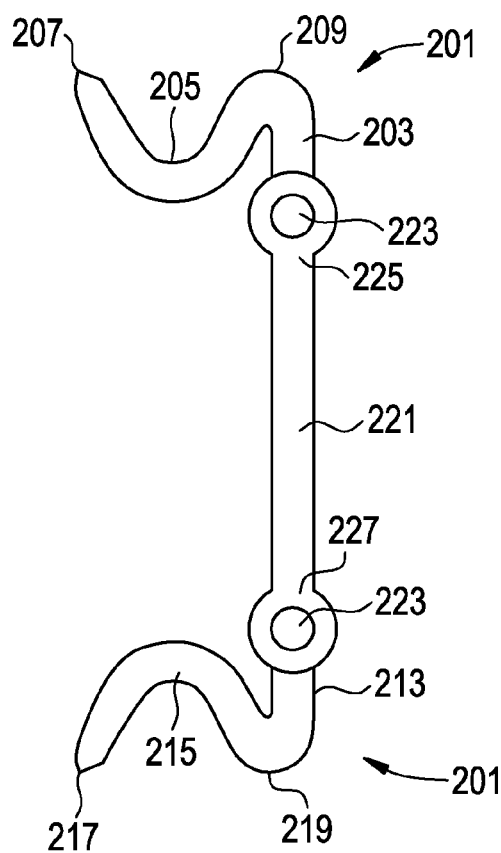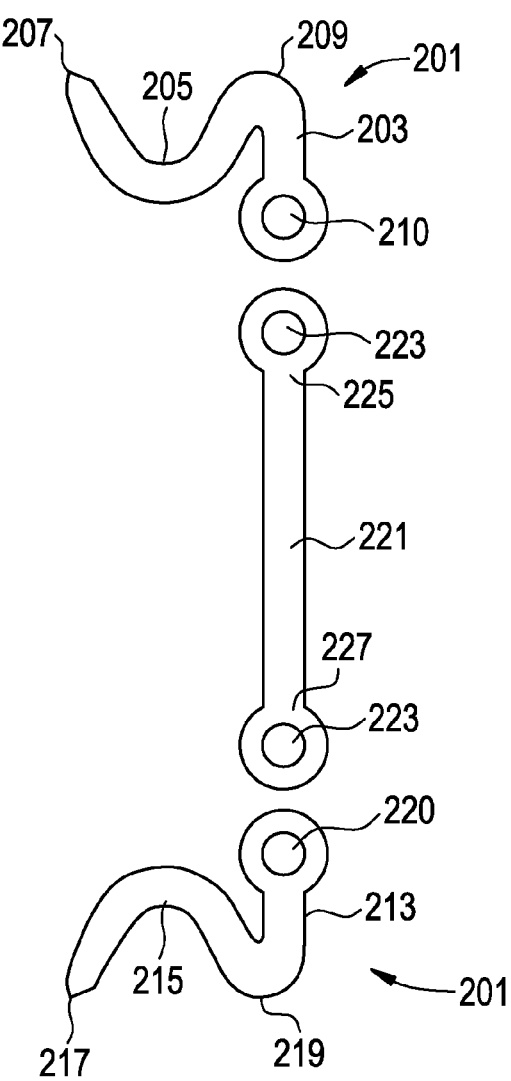

S-SHAPED INTERSPINOUS PROCESS SPACER HAVING TIGHT ACCESS OFFSET HOOKS

CONTINUING DATA

This continuation-in-part patent application claims priority from co-pending U.S. Ser. No. 12/055,757, filed Mar. 26, 2008, entitled "Interspinous Process Spacer Having Tight Access Offset Hooks" (Hawkins).

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint.

In some cases, when a patient having a collapsed disc moves in extension (e.g., leans backward), the posterior portion of the annulus fibrosis or folding of the ligamentum flavum may further compress and extend into the spinal canal. This condition, called "spinal stenosis", narrows the spinal canal and causes impingement of tissue upon the spinal cord, thereby producing pain.

There have been numerous attempts to provide relief for these afflictions by providing a spacer that inserts between adjacent spinous processes present in the posterior portion of the spinal column. This spacer essentially lifts the upper spinous process off of the lower spinous process, thereby relieving stenosis. In general, these interspinous implants are adapted to allow flexion movement in the patient, but resist or limit extension.

U.S. Pat. No. 6,068,630 ("Zuchermann") discloses a spinal distraction implant that alleviates pain associated with spinal stenosis by expanding the volume in the spinal canal or neural foramen. Zuchermann discloses a plurality of implants having a body portion and lateral wings. The body portion is adapted to seat between the adjacent spinous processes, while the wings are adapted to prevent lateral movement of the body portion, thereby holding it in place between the adjacent spinous processes. The designs disclosed in FIGS. 15, 80 and 84 of Zuchermann comprise central body having an integral wing. Although the Zuchermann device achieves spinal distraction, it nonetheless possesses some limitations. First, since the Zuchermann central bodies have at least one integral wing, the clinician may encounter difficulty in sizing the central body independently of delivering the lateral wings. Second, the expansive geometry of the disclosed devices may not lend itself to minimally invasive surgical techniques seeking to conserve muscle mass and soft tissue in the regions adjacent the spinous processes.

U.S. Pat. No. 7,029,472 (Fortin) discloses a distraction device enabling management of the evolving deformation of the trunk of a child during growth. The device is easy to implant on account of its compact shape and includes two rods which can be bent and deformed on the ends thereof and which are mounted on a central adjusting member which is provided with a small hole for engaging a small tool that is designed to adjust the distance separating the elements for attachment to the bone. The inventive device can be locked in a position which is determined by the tightening of two screws which are disposed on the adjusting device.

U.S. Pat. No. 5,989,251 (Nichols) discloses an apparatus is disclosed for connecting first and second elongated spaced apart spinal rods to one another which includes a first connector having structure to engage a first spinal rod at a location along the length thereof and an elongated beam having an axis extending in a direction transverse to the first spinal rod, a second connector having structure to engage a second spinal rod at a location adjacent the first connector and including a reception portion projecting in a direction transverse to the second spinal rod and defining a channel for receiving the elongated beam of the first connector, and a locking member dimensioned and configured to engage the channel along the axis of the beam and secure the position of the beam with respect thereto.

U.S. Pat. No. 6,589,243 (Viart) discloses a posterior spinal osteosynthesis device for providing a transverse connection between two vertebral rods extending along a spinal segment wherein the device includes pairs of hooks adapted to laterally engage the vertebra with each pair being connected by a pair of parallel rods which are elastically bent to form a transverse arc whose ends are engaged in bores within the hooks.

SUMMARY OF THE INVENTION

In accordance with the present invention, there is provided an interspinous spacer comprising:
 a) a spinal connecting member (such as a rod),
 b) a first hook having a first body portion having a first outer face, a first inner face defining an inner plane, a first medial face, a first throughhole extending from the first outer face to the first inner face, and a first flange having i) a proximal portion extending medially and inwardly from the inner plane, ii) a curved intermediate portion, and iii) a distal portion extending medially from the curved intermediate portion and towards the inner plane,
 c) a second hook having a second body portion having a second outer face, a second inner face defining an inner plane, a second medial face, a second throughhole extending from the second outer face to the second inner face, and a second flange having i) a proximal portion extending medially and inwardly from the inner plane, ii) a curved intermediate portion, and iii) a distal portion extending medially from the curved intermediate portion and towards the inner plane,
wherein the rod extends through each of the throughholes so that the hooks are slidably disposed on the rod,
wherein the hooks are oriented so that their inner faces oppose each other.

Preferably, the rod extends through each of the throughholes so that the hooks are slidably disposed on the rod, and the concave surfaces of the hooks are oriented to face each other.

Preferably, the rod extends through each of the throughholes so that the hooks are slidably disposed on the rod, the proximal, intermediate and distal portions of the first flange form a first flange plane, the proximal, intermediate and distal portions of the second flange form a second flange plane, and the first flange plane is different from the second flange plane.

In use, a small incision is first made on one side of the interspinous processes of a functional spinal unit in order to provide lateral access to the gap located between adjacent spinous processes. Preferably, the incision used to provide lateral access to the gap spares the supraspinous ligament that connects the spinous processes.

Concurrently, outside the patient, the dual hooks of the interspinous process spacer are placed onto a spinal rod of appropriate length in an orientation whereby the convex faces of the hooks face each other. The hooks are then brought to together so that the ends of the curved flange portions of each hook meet each other. This requires that the convex faces of the hooks move past each other somewhat as the hooks are moved towards the center of the rod.

The device is then placed in this condition into the incision and oriented so that the rod is substantially parallel with the spinal cord, the hooks are essentially in a coronal plane, and the ends of the flange portions approach the gap between the opposed inner portions of two adjacent interspinous processes. The distal ends of the flanges are then laterally inserted into the gap so that the distal convex portion of the first flange contacts and bears against the upper spinous process and the distal convex portion of the second flange contacts and bears against the lower spinous process. Next, the device is further advanced into the gap without widening the gap. Further inserting the device into the gap causes the concave intermediate portion of the second flange to contact the inner portion of the upper spinous process, and the concave intermediate portion of the first flange to contact the inner portion of the lower spinous process. In its final position, the concave intermediate portion of the second flange bears against the inner portion of the upper spinous process, while the concave intermediate portion of the first flange bears against the inner portion of the lower spinous process. When this final position is reached, the sets screws are advanced so as to lock each hook on the rod to fix the desired bearings of the concave intermediate portion of the each flange with the respective inner portion of each spinous process.

There are many advantages to the dual hook interspinous process spacer of the present invention.

Typically, and as shown above, the hooks of the device are inserted as a pair into the gap between the spinous processes. However, in other embodiments, the hooks can be inserted separately, one after the other. Even when inserted separately, the offset, interlocking nature of the hooks prevents the distal ends of the hooks from contacting each other. Because the ends of these hooks are aligned in a side-by-side manner, and not in an axial manner, just a single hook thickness enters the gap between adjacent spinous processes.

Typically, once the surgeon has achieved placed the hooks in their desired distracted positions, the positions are then fixed by locking each such hook onto a spinal rod. The locking is usually achieved by tightening a set screw located on the hook onto the rod. However, other locking features such as outer nuts, swage/crimp mechanisms, cam locks and press fit can be used to lock the positions of the hooks Connecting members could be ridged or flexible, telescoping or energy storing. They could be plates, rods, springs, tubes, or unibody (as a protuberance) with one of the hooks. They could allow rotation but not translation.

In some embodiments, each hook is placed on the rod and one hook is immediately tightened prior to inserting the device into the incision. In this condition, the untightened hook is allowed to float vis-a-vis the tightened hook. Insertion and distraction are then carried out with the hooks in this condition and the floating hook is then tightened once distraction is achieved.

In other embodiments, only the hook components of the device are inserted into the incision. They are initially mounted onto an instrument that provides them with the desired insertion orientation, and also allows them to spread apart in order to distract the adjacent spinous processes. In this embodiment, the connecting members can then be attached, and then locked to the hooks in a subsequent step.

In yet another embodiment, an instrument could be provided that could hold the hooks separately from the rod so that both hooks could float on a centered rod. This would allow the entire assembly to be inserted in one step.

In some embodiments, connecting members could bridge a single pair of hooks, for relieving stenosis at a single level, while in other embodiments, connecting members could bridge multiple pairs of hooks for relieving stenosis at multiple levels. In some two level embodiments, two pairs of hooks are used. In some three level embodiments, three pairs of hooks are used. In some multi-level embodiments, two hooks could be provided at a first level, while a single hook could be provided at a second level. In other multi-level embodiments, a first single hook is used at a first level and a second single hook is used at a second level.

In some embodiments, the distraction instruments are designed to distract a single level. In other embodiments, the distraction instruments are designed to distract over multiple levels.

It is often the case that there is a variation in the bony geometry of the spinous processes that does not lend itself to the straightforward geometry of the device of FIG. 1. In some embodiments, after insertion or at differing levels, the hooks can be rotated about the connecting member's longitudinal axis in order to accommodate variations in bony geometry, and then locked in their desired position. Alternatively, the hooks of the present invention could have a swivel mechanism that allows the surgeon to adjust to variations in bony geometry, In another embodiment, the hooks can be made of flexible materials so that they have flexible/spring-like qualities.

The devices of the present invention can be designed to accommodate modularity. For example, the hooks of the present invention can be designed with different throats, blade widths, or connecting feature attachment angles, etc. For example, a thin superior element can be connected to a wide inferior element; a rib could be connected to a transverse process; and a sacral lip could be connected to a lamina.

In some embodiments, the hooks of the present invention may have extension tabs for percutaneous manipulation. Tabs could be break off or snap on/off. Instruments could attach by twisting, clamping, screwing.

DESCRIPTION OF THE FIGURES

FIGS. 9a-9b disclose the lateral insertion of the spacer of FIG. 8a into an interspinous space.

FIGS. 10-10b disclose assembled and exploded configurations of the multi-level spacer of the present invention having a connecting rod.

DETAILED DESCRIPTION OF THE INVENTION

Figure 1A:
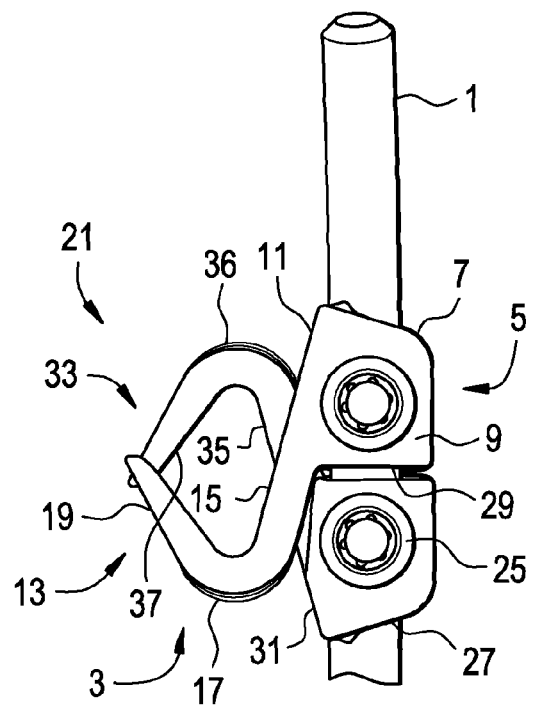
FIGS. 1a-1e show different views of the spacer of the present invention.
Figure 1B:
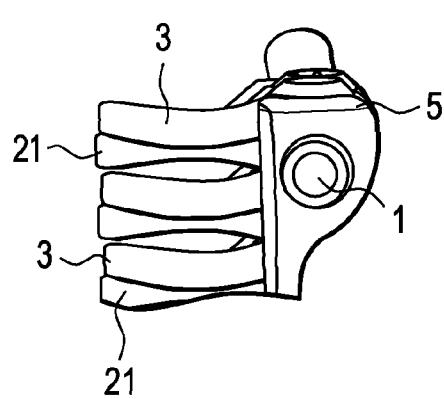
Figure 1C:
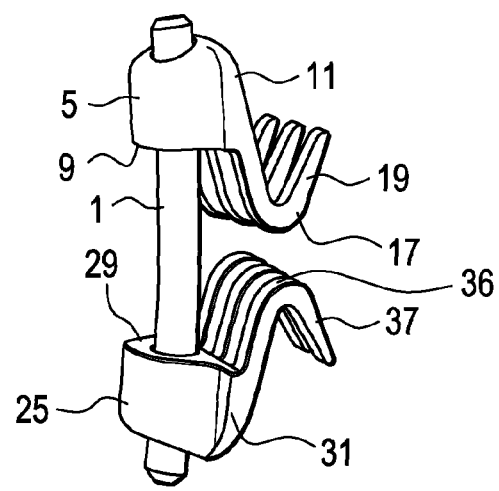
Figure 1D:
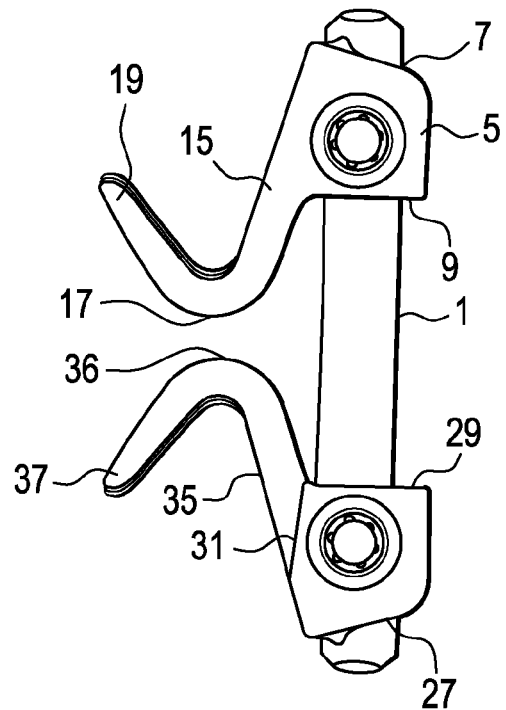

Now referring to FIGS. 1a-1d, there is provided an interspinous spacer comprising:
a) a spinal connecting member, such as a rod 1,
b) a first hook 3 having a first body portion 5 having a first outer face 7, a first inner face 9 defining an inner plane, a first medial face 11, a first throughhole extending from the first outer face to the first inner face, and a first flange 13 having i) a proximal portion 15 extending medially and inwardly from the inner plane, ii) a curved intermediate portion 17, and iii) a distal portion 19 extending medially from the curved intermediate portion and towards the inner plane,
c) a second hook 21 having a second body portion 25 having a second outer face 27, a second inner face 29 defining an inner plane, a second medial face 31, a second throughhole extending from the second outer face to the second inner face, and a second flange 33 having i) a proximal portion 35 extending medially and inwardly from the inner plane, ii) a curved intermediate portion 36, and iii) a distal portion 37 extending medially from the curved intermediate portion and towards the inner plane,
wherein the rod extends through each of the throughholes so that the hooks are slidably disposed on the rod, and
wherein the hooks are oriented so that their inner faces oppose each other.

A preferred method of implanting the device of the present invention is presented in FIGS. 2-6. Now referring to FIG. 2a, there is provided a pair of hooks 51 of the present invention that are pre-loaded onto a pair of holder instruments 53 and provided in a separated condition. Now referring to FIG. 2b, there is provided a pair of hooks 51 of the present invention that are pre-loaded onto a pair of holder instruments 53 and provided in a interdigitated condition. A knob 55 is provided on the proximal end of each holder instrument in order to tighten the hooks onto the distal ends of the holder instruments. In this FIG. 2a-b, this knob is located at the proximal end 57 of the holder instrument, but it could also be located at the distal end 59 as well. In other embodiments, the knob can be replaced with other tightening means, such as a lever or a snap-on. In some embodiments, the cannulated shaft of the holding instrument possesses a pair of slots 59 running along opposite sides of the instrument. These slots allow the rod component of the device to be pre-loaded onto the holder instruments and tightened into one of the hooks.

Figure 3:
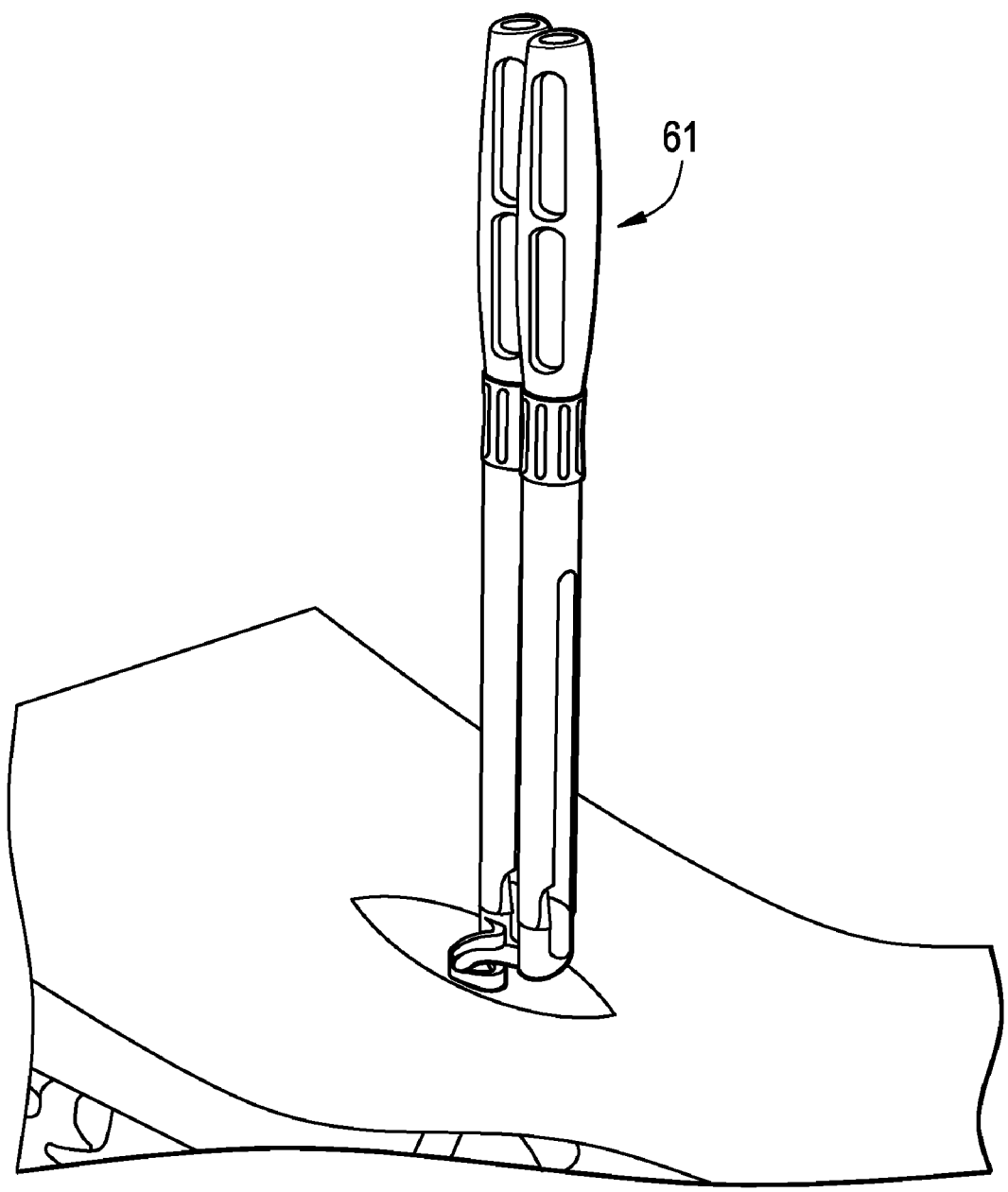
FIG. 3 shows simultaneous hook placement into the spine.

Now referring to FIG. 3, insertion of a pair of interdigitated hooks of the present invention into the spinal anatomy is demonstrated. The handles 61 of the holding instruments are held by the surgeon as the joined hooks are carefully inserted together between adjacent spinous processes. The holding instruments are adapted to allow these hooks to float in one direction (or be just gently guided). In this FIG. 3, the hooks are allowed to float along the cephalad/caudal axis, and the surgeon can manipulates them along the medial/lateral axis. In some embodiments, the rod of the present invention (not shown) can be attached by securing it to one of the hooks.

Figure 4:
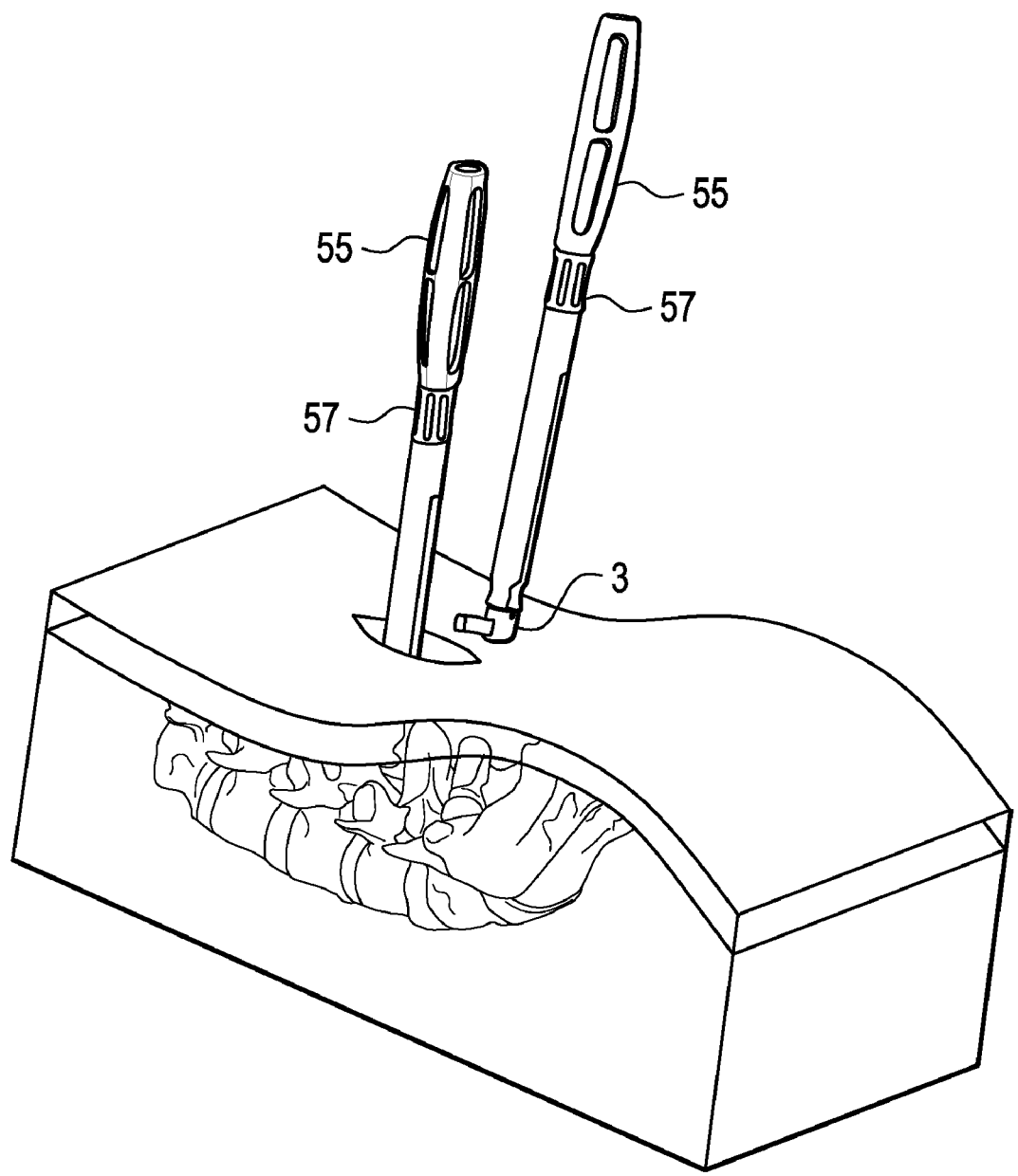
FIG. 4 shows individual hook placement into the spine.

Now referring to FIG. 4, an individual hook may be implanted into the spinal anatomy by itself. Once the individual hook is implanted, the surgeon may implant its mating hook (not shown), either at the same level or at a different level. The special geometry of these hooks allows the single prong hook to pass through the dual prong hook without their obstructing each other.

Figure 5B:
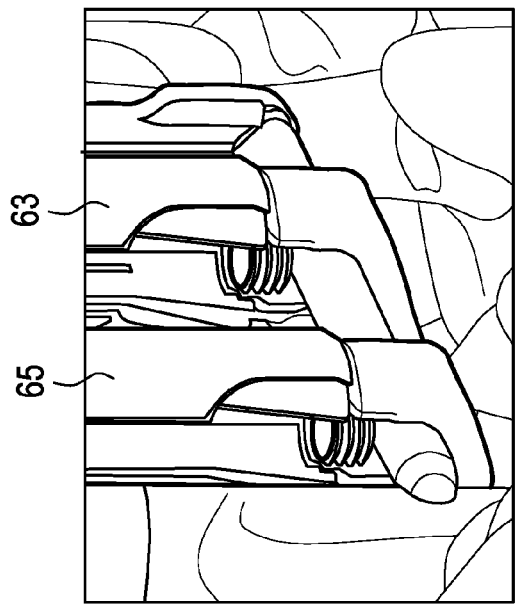
FIG. 5b shows rod approximation, wherein the set screw is the holding feature for securing the rod to the hook.
Figure 5A:
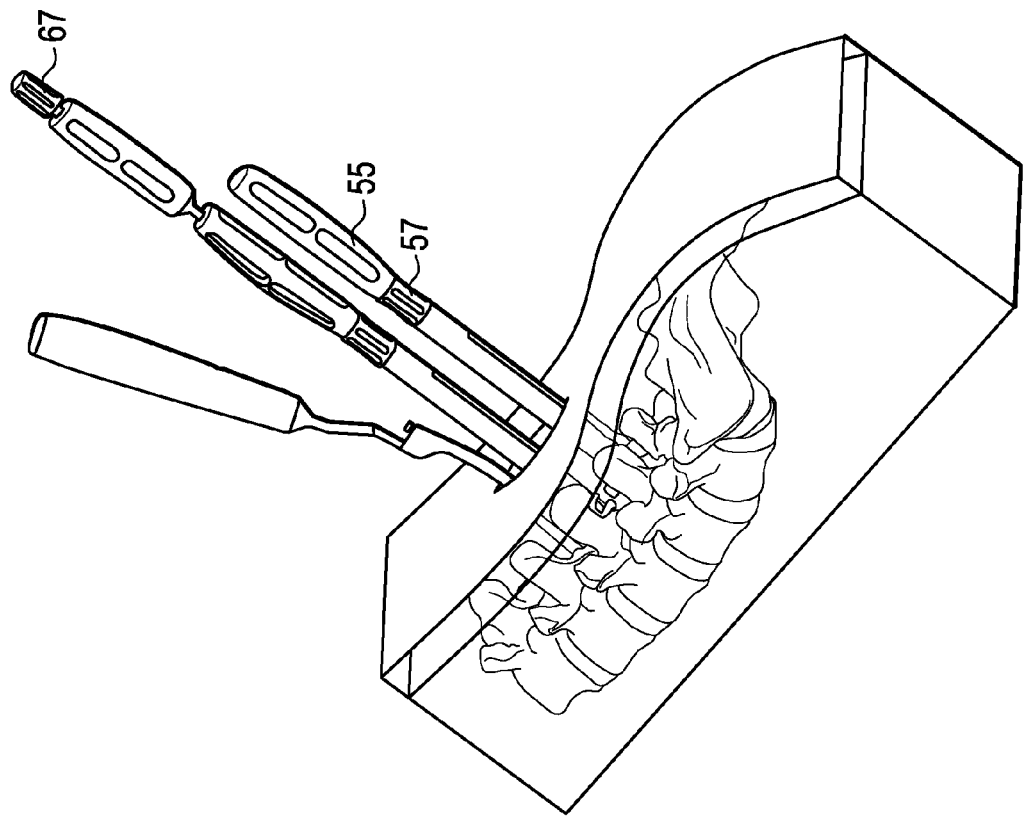
FIG. 5a shows rod approximation, wherein the rod is passed into the hooks either from a cephalad or caudal direction.
Figure 6:
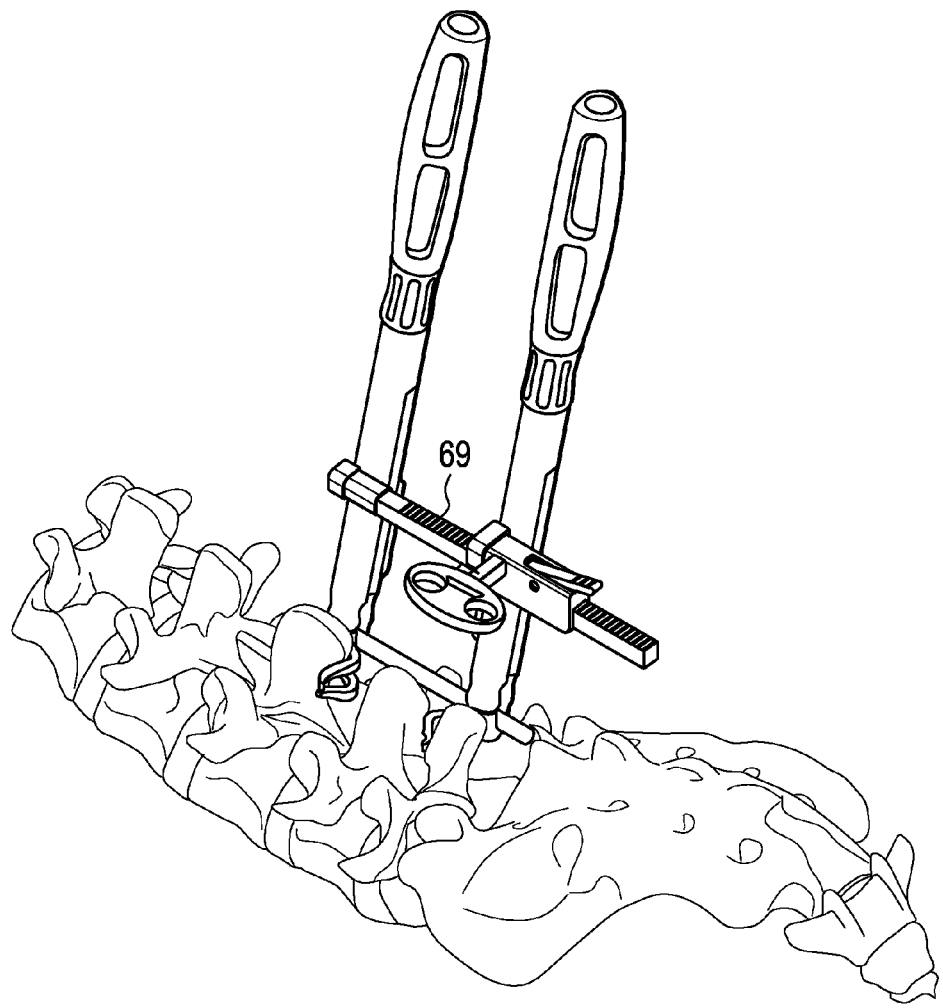
FIG. 6 shows the hooks of the present invention distracting spinous processes over longer distances.

Now referring to FIGS. 5a-b, once the hooks have been implanted, rod approximation is carried out. This rod can be passed into the hooks either from a cephalad or caudal direction (as in FIG. 5a), or from down the middle (between the hook holding instruments). FIG. 5a shows a rod holder patterned after the rod holder of DePuy Spine's VIPER™ system, which holds the rod at its end. Now referring to FIG. 5b, the set screw 63 is the holding feature for securing the rod to the hook. Also shown is a set screw tightening instrument 65 inserted in the superior hook holder, which is canulated to allow the tightening operation. The most proximal knob 67 of the apparatus secures the set screw in the set screw instrument prior to sliding it down the hook holding instrument.

At close distances (e.g., one level), the holding instruments can be forced apart with the use of a simple twisting spreader, by hand, or by using typical squeeze handle distractors. Now referring to FIG. 6, the hooks of the present invention are capable of distracting spinous processes over longer distances. Over longer distances, it is preferred to use a rack-style distractor 69, which has the ability to provide distraction over at least 10 centimeters of separation. Thus, in these long distance embodiments, one or more hooks could be implanted at any level of the spinal anatomy, with all of the hooks being connected through a single rod. Joined pairs of hooks provided at the same level can be distracted, and/or remote pairs of hooks provided at different levels can be distracted. The rack distractor of FIG. 6 can push against the hook holder instruments at both ends, against the hook itself, or against a rod holder at one or both ends.

Figure 1E:
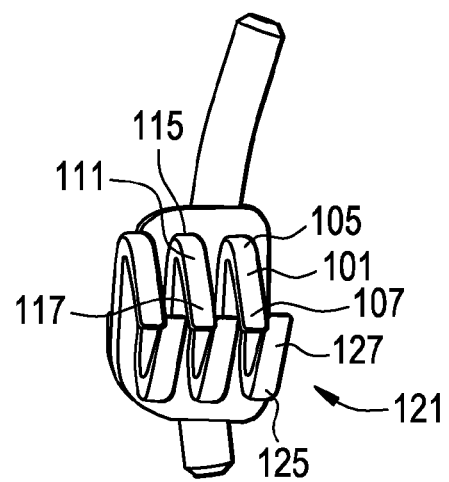
Figure 2A:
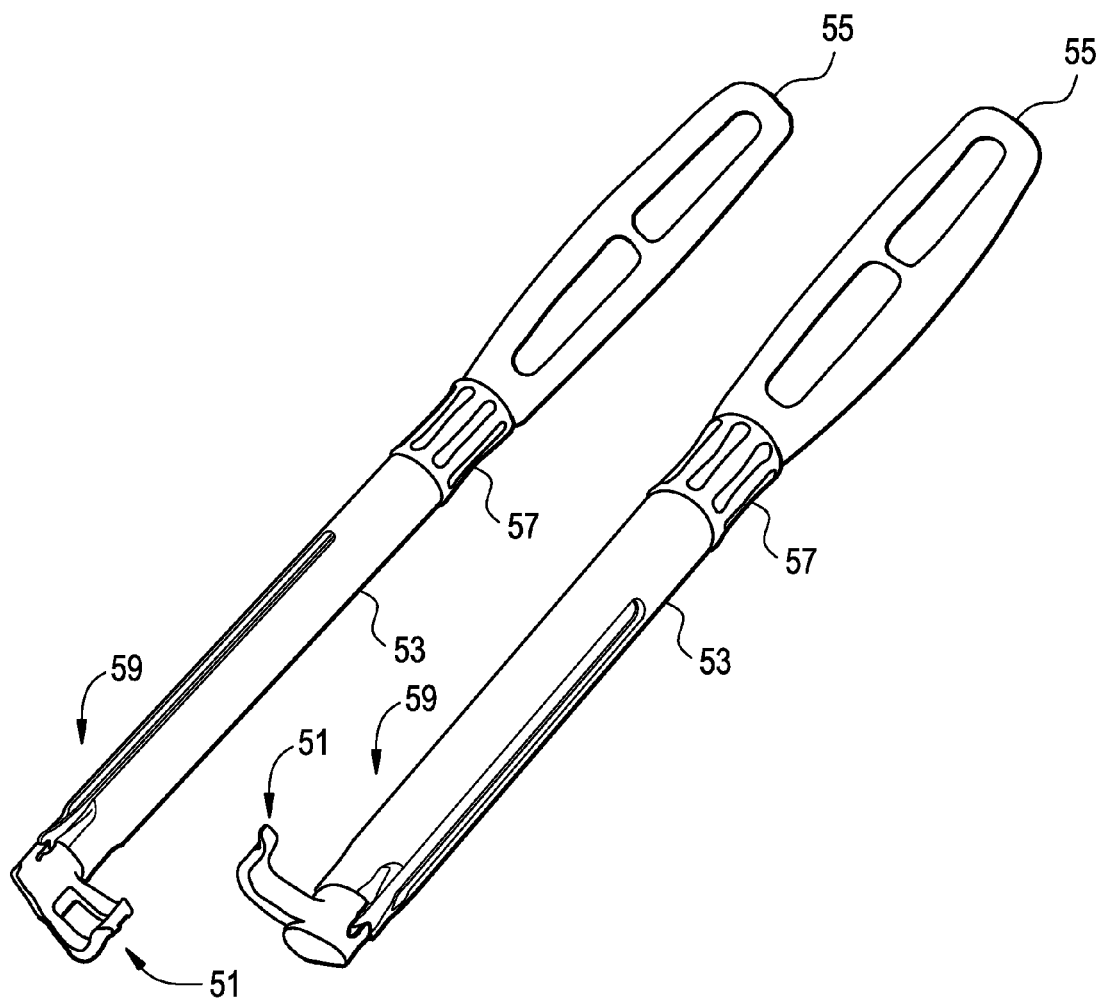
FIG. 2a shows a perspective view of superior and inferior hook extension instruments of the present invention grasping the two hook components of the spacer.
Figure 2B:
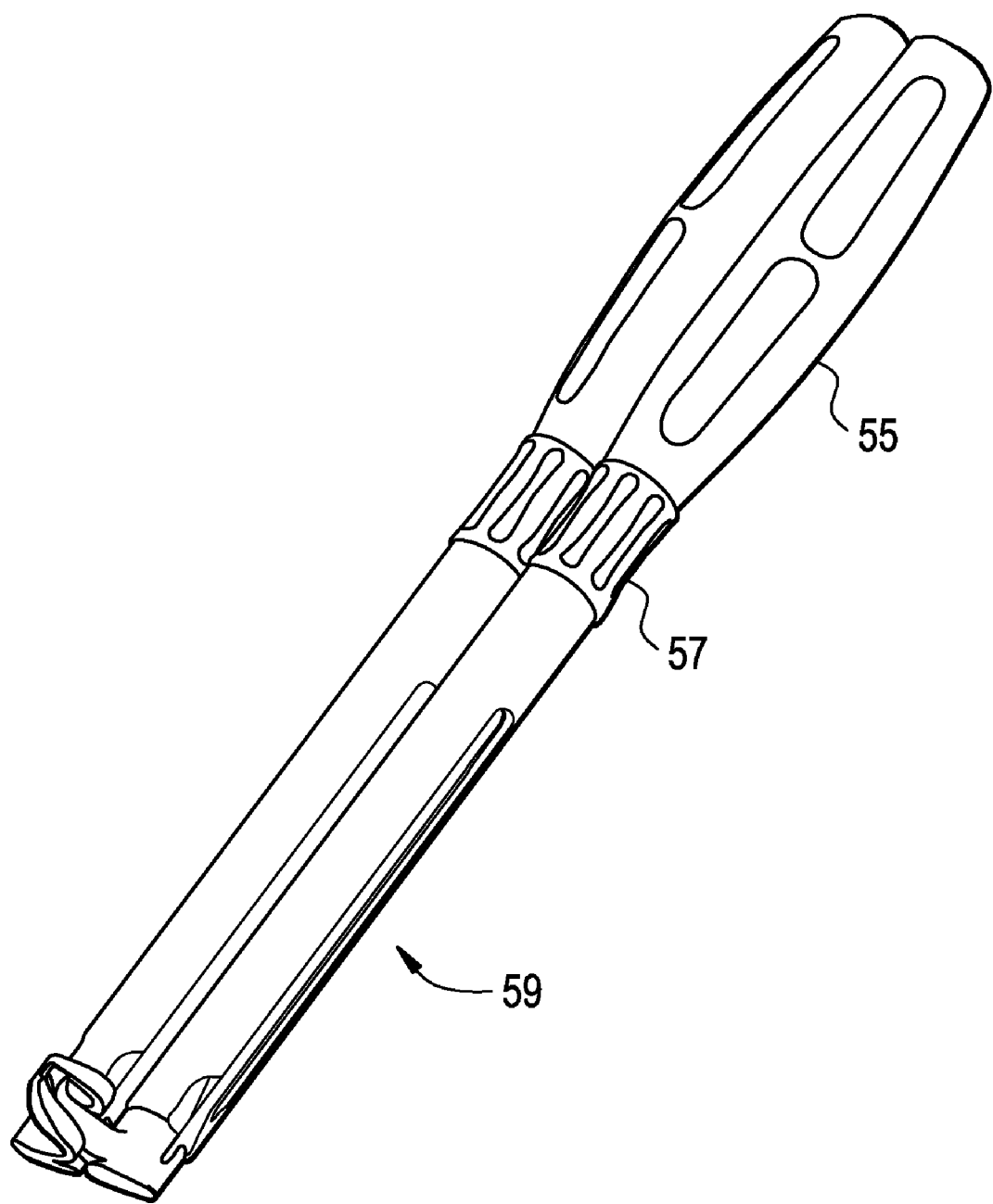
FIG. 2b shows the assemblies of FIG. 2a brought together for simultaneous hook placement.

Now referring to FIG. 1e, preferably, at least one of the hooks has multiple flanges so that the interspinous spacer comprises:
a) a spinal rod,
b) a first hook having a first body portion having a first outer face, a first inner face defining an inner plane, a first medial face, a first throughhole extending from the first outer face to the first inner face, a first flange 101 having i) a proximal portion extending medially, ii) a curved intermediate portion 105 forming a concave surface, and iii) a distal portion 107 extending medially from the curved intermediate portion, a second flange 111 having i) a proximal portion extending medially, ii) a curved intermediate portion 115 forming a concave surface, and iii) a distal portion 117 extending medially from the curved intermediate portion,
c) a second hook having a second body portion having a second outer face, a second inner face defining an inner plane, a second medial face, a second throughhole extending from the second outer face to the second inner face, and a third flange 121 having i) a proximal portion extending medially, ii) a curved intermediate portion 125 forming a concave surface, and iii) a distal portion 127 extending medially from the curved intermediate portion,
wherein the rod extends through each of the throughholes so that the hooks are slidably disposed on the rod.

Figure 7:
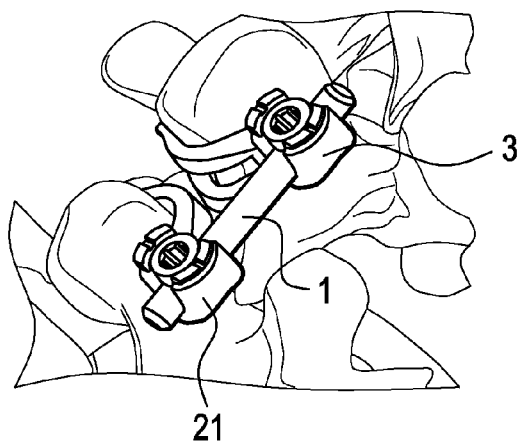
FIG. 7 shows the device of the present invention implanted in the interspinous space.
Figure 8A:
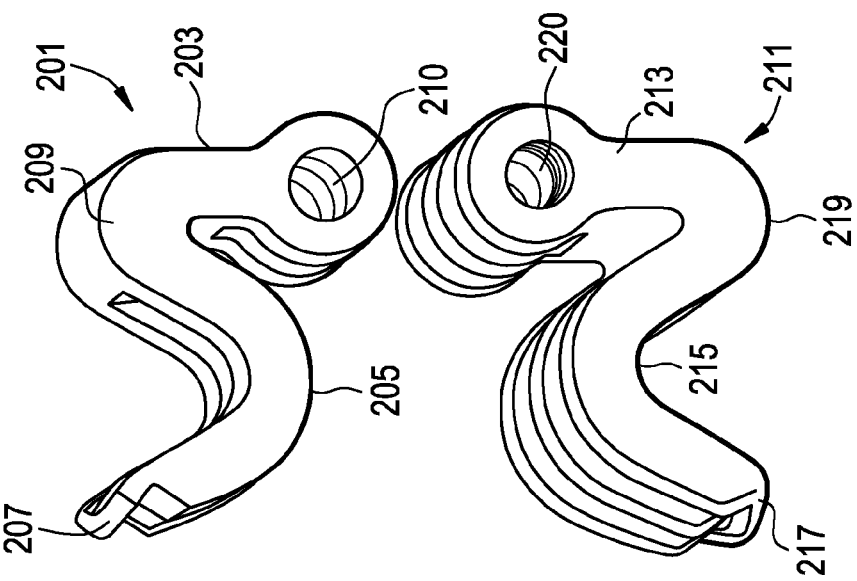
FIGS. 8a-8c disclose collapsed, expanded and exploded configurations of the spacer of the present invention having S-shaped hooks.
Figure 8B:
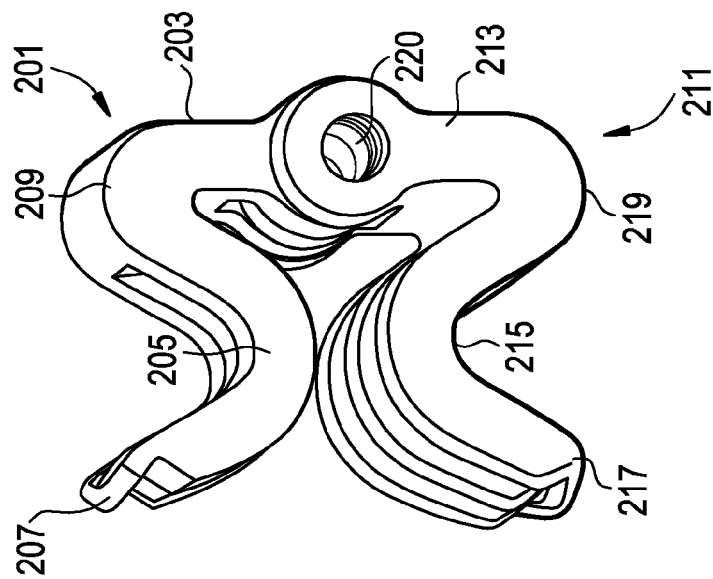
Figure 8C:
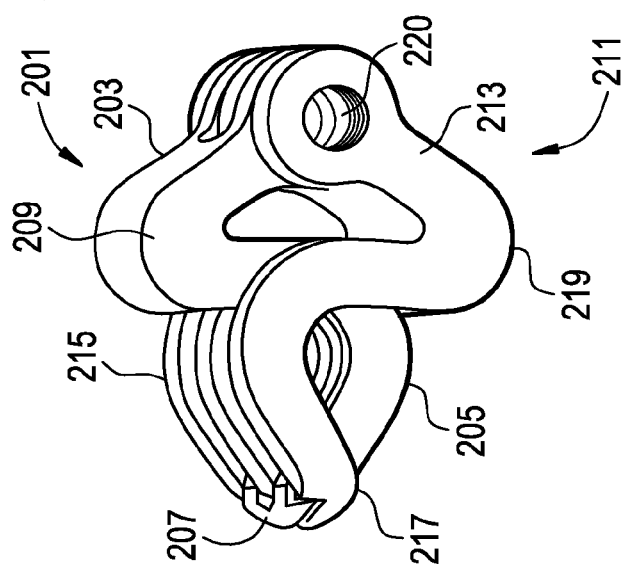

Lastly, FIG. 7 shows the device of the present invention comprising spinal rod 1, first hook 3, and second hook 21 implanted in the interspinous space.

In other embodiments of the present invention, two hooks of the present invention could be used to respectively engage a spinous process and a lamina. For example, in the L5-S1 region, there can be a first hook connected to the spinous process and a second hook having an intralaminar connection.

In other embodiments of the present invention, a drug-eluting device may be used in conjunction with the present invention or incorporated into or onto the device of the present invention. In one embodiment, a drug eluting device is incorporated into or onto the rod. The drugs may include anti-inflammatory or pain-killing drugs.

In other embodiments, the device of the present invention may be used as a rib spreader for correcting rib deformities, particularly in pediatric cases.

The hook and rod component of the device of the present invention could be metal, plastic, or ceramic. They could be biodegradable. They could be coated for ingrowth or porous for nutrition.

If a metal is chosen as the material of construction for a component, then the metal is preferably selected from the group consisting of nitinol, titanium, titanium alloys (such as Ti-6Al-4V), chrome alloys (such as CrCo or Cr—Co—Mo) and stainless steel.

If a polymer is chosen as a material of construction for a component, then the polymer is preferably selected from the group consisting of polycarbonates, polyesters, (particularly aromatic esters such as polyalkylene terephthalates, polyamides; polyalkenes; poly(vinyl fluoride); PTFE; polyarylethyl ketone PAEK; and mixtures thereof.

In some embodiments, the tube is made of a stainless steel alloy, preferably BioDur® CCM Plus® Alloy available from Carpenter Specialty Alloys, Carpenter Technology Corporation of Wyomissing, Pa. In some embodiments, the tube is made from a composite comprising carbon fiber. Composites comprising carbon fiber are advantageous in that they typically have a strength and stiffness that is superior to neat polymer materials such as a polyarylethyl ketone PAEK. In some embodiments, the tube is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
a) 40-99% (more preferably, 60-80 vol %) polyarylethyl ketone (PAEK), and
b) 1-60% (more preferably, 20-40 vol %) carbon fiber,
wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

Now referring to FIGS. 8a-8c and 9a-9b, there is provided an interspinous spacer comprising:
a) a first spinal connecting member (not shown),
b) a first hook 201 comprising a first substantially S-shaped flange 203 having i) a distal concave portion 205 forming a first distal tip 207 and ii) a proximal convex portion 209 forming a first proximal throughhole 210 extending therethrough, and
c) a second hook 211 comprising a second substantially S-shaped flange 213 having i) a distal concave portion 215 forming a second distal tip 217 and ii) a proximal convex portion 219 forming a second proximal throughhole 220 extending therethrough,
wherein the first spinal connecting member extends through each of the throughholes to connect the hooks.

FIGS. 8a-8c and 9a-9b disclose a spinal implant to be used as a spacer between interspinous processes. The implant utilizes two hooks connected at the one end with a lockable joint. The implant is initially laterally inserted in a collapsed configuration (FIG. 9a). In this position, the two opposite distal tips of the hooks are touching each other, creating a "bullet-nosed" tip that requires only a minimal entry height. Thus, the tip geometry promotes easy insertion of the implant into the interspinous ligament. After the initial entry of the distal tips, simply pushing the spacer into the interspinous process space opens the implant as the implant is pushed through the interspinous space. After initial insertion, the hooks are rotated about each other about the joint to expand the spacer (FIG. 9b). A user can adjust the implant to form a desired height; and the joint is then locked in that position to maintain that height.

The S-shaped nature of the implant adds a spring to flange, which, in its deployed (opened) position, allows the implant to bend or flex a little. When a compressive force is applied to the hooks, the implant can bend a little to slightly decrease the distance between the hooks; thus acting like a spring that restores energy. The amount of damping (and spring) force in the implant can be adjusted by varying selected design parameters, including the implant material, the distance between the hook and the joint, the cross-sectional geometry of the hook, and the overall height of the implant.

Therefore, in accordance with the present invention, there is provided an interspinous spacer comprising:
a) a first spinal connecting member,
b) a first hook comprising a first substantially S-shaped flange having i) a distal concave portion forming a first distal tip and ii) a proximal convex portion forming a first proximal throughhole extending therethrough, and
c) a second hook comprising a second substantially S-shaped flange having i) a distal concave portion forming a second distal tip and ii) a proximal convex portion forming a second proximal throughhole extending therethrough,
wherein the first spinal connecting member extends through each of the throughholes to connect the hooks.

Now referring to FIGS. 10a-10b, there is provided an interspinous spacer comprising:
a) first and second spinal connecting members (not shown),
b) a first hook 201 comprising a first substantially S-shaped flange 203 having i) a distal concave portion 205 forming a first distal tip 207 and ii) a proximal convex portion 209 forming a first proximal throughhole 210 extending therethrough, and
c) a second hook 211 comprising a second substantially S-shaped flange 213 having i) a distal concave portion 215 forming a second distal tip 217 and ii) a proximal convex portion 219 forming a second proximal throughhole 220 extending therethrough, d) a spinal rod 221 having a throughhole 223 at each of a first 225 and second 227 end thereof, wherein the first spinal connecting member extends through the throughhole of the first hook and the throughhole of the first end of the spinal rod, wherein the second spinal connecting member extends through the throughhole of the second hook and the throughhole of the second end of the spinal rod.

FIGS. 10a-10b disclose assembled and exploded embodiments of the multi-level spacer of the present invention having a connecting rod. In some embodiments, as in FIGS. 10a-b, a spinal rod can be inserted between the two hooks to accommodate multi-level usage. An upper hook can be joined at its proximal end to the upper end of the rod, and a lower hook can be joined at its proximal end to the lower end of the rod. Moreover, a kit can be provided with different shapes of hooks and different height of rods. A user can then assemble various hooks and rods to fit the various anatomies and heights of the patient.

Therefore, in accordance with the present invention, there is provided an interspinous spacer comprising:

a) first and second spinal connecting members, b) a first hook comprising a first substantially S-shaped flange having i) a distal concave portion forming a first distal tip and ii) a proximal convex portion forming a first proximal throughhole extending therethrough, c) a second hook comprising a second substantially S-shaped flange having i) a distal concave portion forming a second distal tip and ii) a proximal convex portion forming a second proximal throughhole extending therethrough, d) a spinal rod having a throughhole at each of a first and second end thereof, wherein the first spinal connecting member extends through the throughhole of the first hook and the throughhole of the first end of the spinal rod, wherein the second spinal connecting member extends through the throughhole of the second hook and the throughhole of the second end of the spinal rod.

Figure 11:
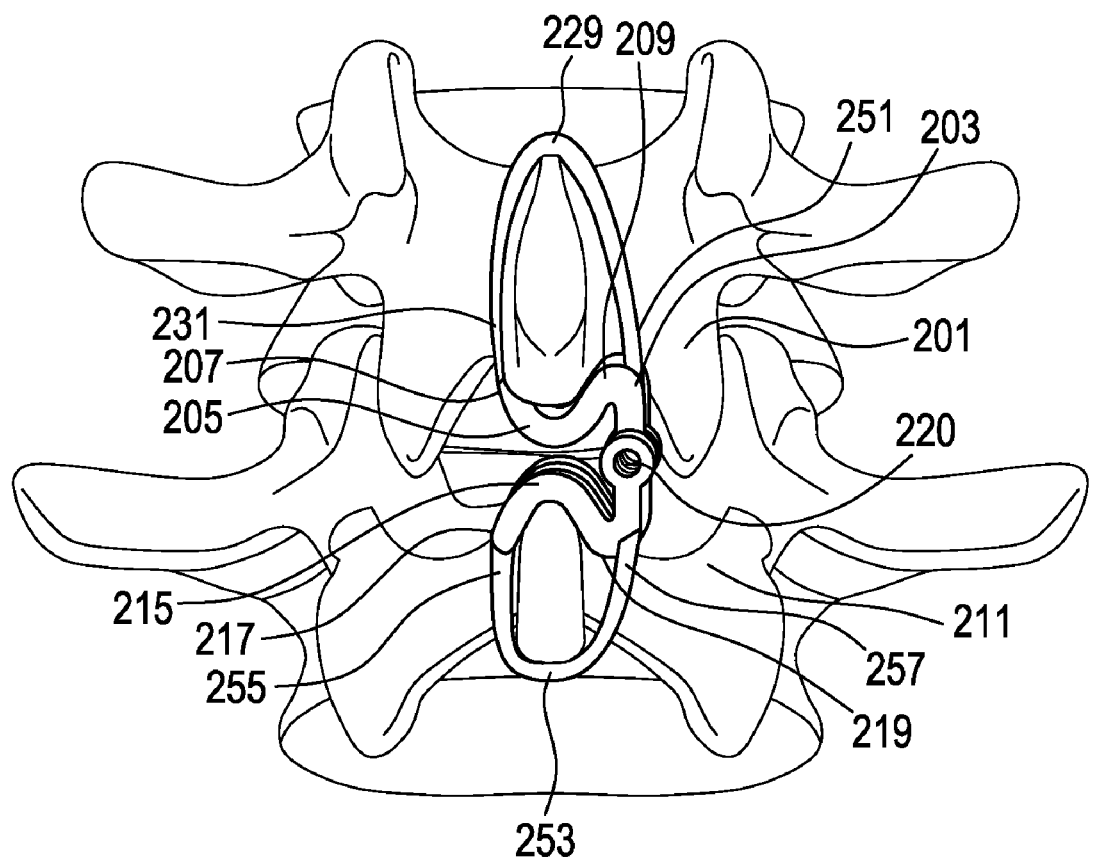
FIG. 11 discloses the spacer of the present invention having two flexible straps.

Now referring to FIG. 11, there is provided an interspinous spacer comprising:

a) a spinal connecting member (not shown), b) a first hook 201 comprising a first flange 203 having i) a first distal concave portion 205 forming a first distal tip 207 and ii) a first proximal portion 209 forming a first proximal throughhole 210 extending therethrough, and, c) a second hook 211 comprising a second flange 213 having i) a second distal concave portion 215 forming a second distal tip 217 and ii) a second proximal portion 219 forming a second proximal throughhole 220 extending therethrough, and d) a first flexible strap 229 having a first 231 and second 251 end, wherein the first end of the first flexible strap is attached to the first distal tip of the first hook, and the second end of the first flexible strap is attached to the first proximal portion of the first hook.

e) a second flexible strap 253 having a first 255 and second 257 end, wherein the first end of the second flexible strap is attached to the second distal tip of the second hook, and the second end of the flexible strap is attached to the second proximal portion of the second hook, wherein the spinal connecting member extends through each of the throughholes to connect the hooks.

If it is desirable for the implant to resist flexion of the spine (i.e., wherein the spinous processes move away from each other), flexible straps can be looped around the spinous process and attached to the implant, as shown in FIG. 11. FIG. 11 discloses the spacer of the present invention having two flexible straps. These straps are initially respectively attached to the distal tips of the hooks. After insertion of the implant into interspinous process space, the straps are then looped around the respective adjacent spinous processes, and finally attached to the implant again. The tension in the straps can be adjusted to accommodate the amount of flexion allowed.

Therefore, in accordance with the present invention, there is provided an interspinous spacer comprising:

a) a spinal connecting member, b) a first hook comprising a first flange having i) a first distal concave portion forming a first distal tip and ii) a first proximal portion forming a first proximal throughhole extending therethrough, c) a second hook comprising a second flange having i) a second distal concave portion forming a second distal tip and ii) a second proximal portion forming a second proximal throughhole extending therethrough, and d) a flexible strap having a first and second end, wherein the first end of the flexible strap is attached to the first distal tip of the first hook, wherein the spinal connecting member extends through each of the throughholes to connect the hooks.

Figure 12:
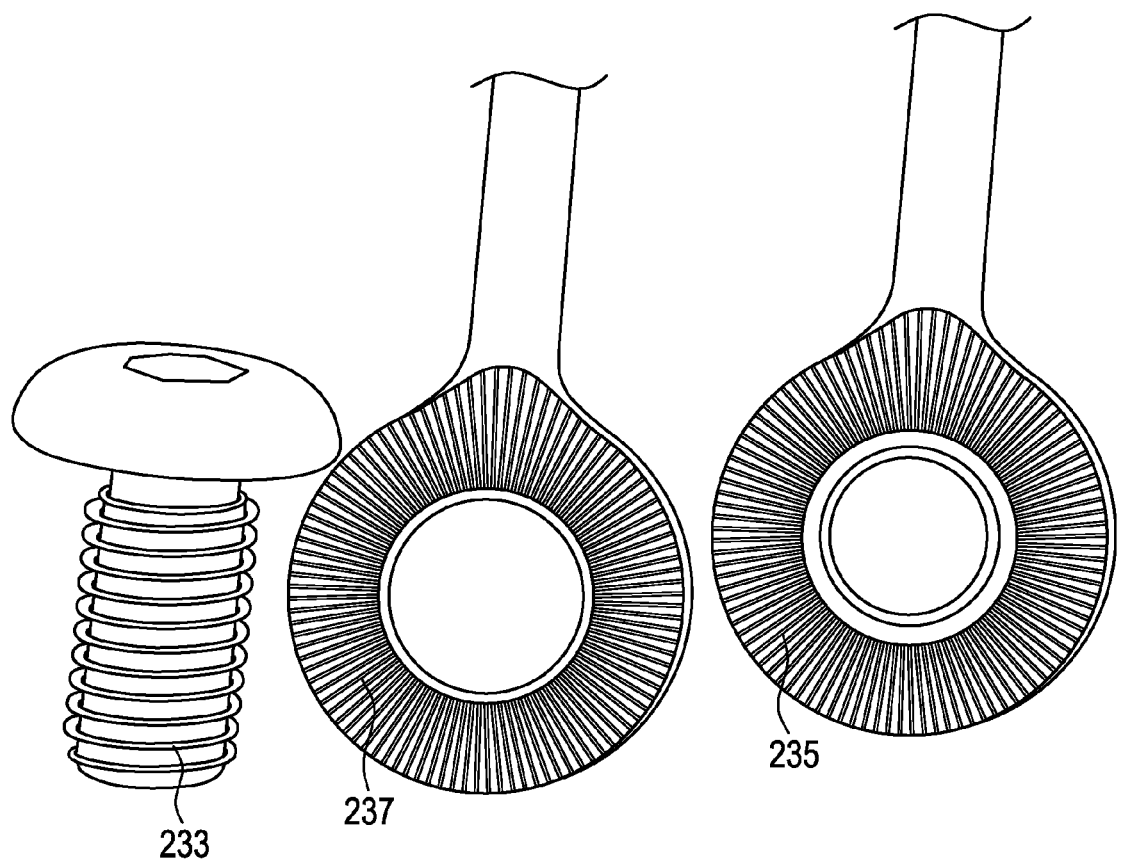
FIG. 12 discloses a screw and the proximal ends of a pair of hooks of the present invention having ridged surfaces and transverse throughholes.

Now referring to FIG. 12, any lockable joint can be used to connect the two hooks together. FIG. 12 discloses the components of a preferred lockable joint: a screw and the proximal ends of a pair of hooks of the present invention having ridged surfaces and transverse throughholes. The main function of the joint is to provide rotational adjustment that can be locked at any desired angle (or height of the implant). One simple joint is a hinge that can be rotated to desired angle, and locked with a spinal connecting member, such as a screw 233. A simple hinge would provide a single degree-of-freedom allowing rotation on the frontal plane. Another example of a useful joint is a universal joint with a locking mechanism. A universal joint would provide motion in two planes; thus, allowing for height adjustment on the frontal plane and rotation on the sagittal plane to accommodate better fit into the spinous process bony contour. Another example of a useful joint is a spherical joint, such as ball-and-socket joint, which has all three degrees-of-freedom allowing rotation in all three axes.

Therefore, in accordance with the present invention, there is provided an interspinous spacer comprising:

a) a first spinal connecting member, b) a first hook comprising a first substantially S-shaped flange having i) a distal concave portion forming a first distal tip and ii) a proximal convex portion forming a first proximal connector, and c) a second hook comprising a second substantially S-shaped flange having i) a distal concave portion forming a second distal tip and ii) a proximal convex portion forming a second proximal connector, wherein the first spinal connecting member contacts each of the connectors to form a lockable joint.

To allow secure locking of the joint, the mating surfaces 235 of the joint can be roughened to increase the friction between them. Furthermore, different geometries can be added on to the mating surfaces to increase the locking strength. As an example, radially ridged surfaces 237 can be added to the mating surfaces. Use of ridged surfaces allows for discrete rotational adjustment, which in turn allows discrete height adjustment.

Therefore, the interspinous spacers of FIGS. 8a-12 have numerous advantages: They allow for an adjustable height that can be locked at any desired height. They provide a collapsed configuration for easy insertion. They are provided in a single-unit design that expands in situ. They have an ability to absorb shocks and compressive forces. They may possess a simple locking mechanism. Lastly, they allow for insertion from one side only, thereby sparing the supraspinous ligament.

Therefore, in accordance with the present invention, there is provided a method of implanting an interspinous spacer, comprising the steps of:
a) providing an interspinous spacer comprising:
   i) a spinal connecting member,
   ii) a first hook comprising a first flange having i) a first distal concave portion forming a first distal tip and ii) a first proximal portion forming a first proximal throughhole extending therethrough, and
   iii) a second hook comprising a second flange having i) a second distal concave portion forming a second distal tip and ii) a second proximal portion forming a second proximal throughhole extending therethrough,
   wherein the spinal connecting member extends through each of the throughholes to connect the hooks,
   wherein the hooks are oriented so that their distal concave portions oppose each other, and
   wherein the hooks are oriented so that their tips substantially meet,
b) providing lateral access to a gap between opposed inner portions of an upper and lower spinous process,
c) laterally inserting the distal tips into the gap.

We claim:
1. An interspinous spacer comprising:
   a) a first spinal connecting member,
   b) a first hook comprising a first substantially S-shaped flange having i) a distal concave portion forming a first distal tip and ii) a proximal convex portion forming a first proximal throughhole extending therethrough, and
   c) a second hook comprising a second substantially S-shaped flange having i) a distal concave portion forming a second distal tip and ii) a proximal convex portion forming a second proximal throughhole extending therethrough,
wherein the first spinal connecting member extends through each of the throughholes to connect the hooks,
wherein the hooks are oriented so that their tips substantially meet,
wherein the hooks are rotated about each other and about the spinal connecting member to expand the spacer.

2. The spacer of claim 1 wherein the first proximal throughhole extends tranversely through
   the first proximal convex portion.

3. The spacer of claim 1 wherein the hooks are oriented so that their distal concave portions oppose each other.

4. The spacer of claim 1 further comprising d) a flexible strap having a first and second end, wherein the first end of the flexible strap is attached to the first distal tip of the first hook, and the second end of the flexible strap is attached to the first proximal portion of the first hook.

* * * * *